US006358698B1

(12) United States Patent
Weiner et al.

(10) Patent No.: US 6,358,698 B1
(45) Date of Patent: Mar. 19, 2002

(54) METHODS OF IDENTIFYING INVERSE AGONISTS OF THE SEROTONIN 2A RECEPTOR

(75) Inventors: David Weiner; Mark R. Brann, both of San Diego, CA (US)

(73) Assignee: Acadia Pharmacueticals Inc., San Diego, CA (US)

( * ) Notice: Subject to any disclaimer, the term of this patent is extended or adjusted under 35 U.S.C. 154(b) by 0 days.

(21) Appl. No.: 09/413,626

(22) Filed: Oct. 6, 1999

Related U.S. Application Data

(60) Provisional application No. 60/103,317, filed on Oct. 7, 1998.

(51) Int. Cl.$^7$ ............................................. G01N 33/567
(52) U.S. Cl. ........................ 435/7.21; 435/7.1; 435/7.2; 436/501
(58) Field of Search ........................ 435/7.1, 7.2, 7.21; 436/501

(56) References Cited

U.S. PATENT DOCUMENTS

| 5,661,024 A | | 8/1997 | Kao et al. ................. 435/240.2 |
| 6,107,324 A | * | 8/2000 | Behan et al. ................ 514/406 |

FOREIGN PATENT DOCUMENTS

| WO | WO 96/17081 | 6/1996 | ............. C12Q/1/68 |
| WO | WO 98/38217 | 9/1998 | ......... C07K/14/705 |
| WO | WO 99/52927 | 10/1999 | ........... C07H/21/04 |

OTHER PUBLICATIONS

Casey et al. Constitutively Active Mutant 5HT2A Receptors, Society For Neuroscience Abstracts 22(3):699.10, Nov. 1996.*

Kehne et al., Preclinical Characterization of the Potential of the Putative Atypical Antipsychotic MDL 100,907 as a Potent 5–HT$_{2A}$ Antagonist with a Favorable CNS Safety Profile, JPET 277:968–981 (1996).

Egan et al., Creation of a Constitutively Activated State of the 5–Hydroxytryptamine$_{2A}$ Receptor by Site–Directed Mutagenesis: Inverse Agonist Activity of Antipsychotic Drugs, JPET 286:85–90 (1998).

Egan et al., Creation of a Constitutively Activated State of the 5–HT$_{2A}$ Receptor by Site–directed Mutagenesis: Revelation of Inverse Agonist Activity of Antagonists, Annals NY Acad. Sci. 861:136–139 (1998).

Pauwels, et al., "Review: Amino Acid Domains Involved in Constitutive Activation of G–Protein–Coupled Receptors," Molecular Neurobiology, 1998, Humana Press, pp. 109–135.

Shenker, et al., "A constitutively activiating mutation of the luteinizing hormone receptor in familial male precocious puberty," Nature, vol. 365, Oct. 14, 1993, pp. 652–654.

Eggerickx, et al., "Molecular cloning of an orphan G–protein–coupled receptor that constitutively activates adenylate cyclase," Biochemical Journal, GB, Portland Press, vol. 309, 1995, pp. 837–843.

Grotewiel, et al., "Receptors Exhibit Constitutive Activity That is Blocked by Inverse Agonist", Faseb Journal, Vo. 8, No. 7, May 21–25, 1994, p. A1319.

* cited by examiner

*Primary Examiner*—John Ulm
(74) *Attorney, Agent, or Firm*—Pillsbury Winthrop LLP

(57) ABSTRACT

The present invention relates to a method of identifying compounds which act as inverse agonists of the 5-HT2A receptor, the method comprising contacting a constitutively active 5-HT2A receptor with at least one test compound and determining any decrease in the level of basal activity of the receptor so as to identify a test compound which is an inverse agonist of the 5-HT2A receptor. Such inverse agonists may be used in the treatment of schizophrenia and related psychoses.

11 Claims, 4 Drawing Sheets

Figure 1. 5HT2A Receptor Responses in R-SAT
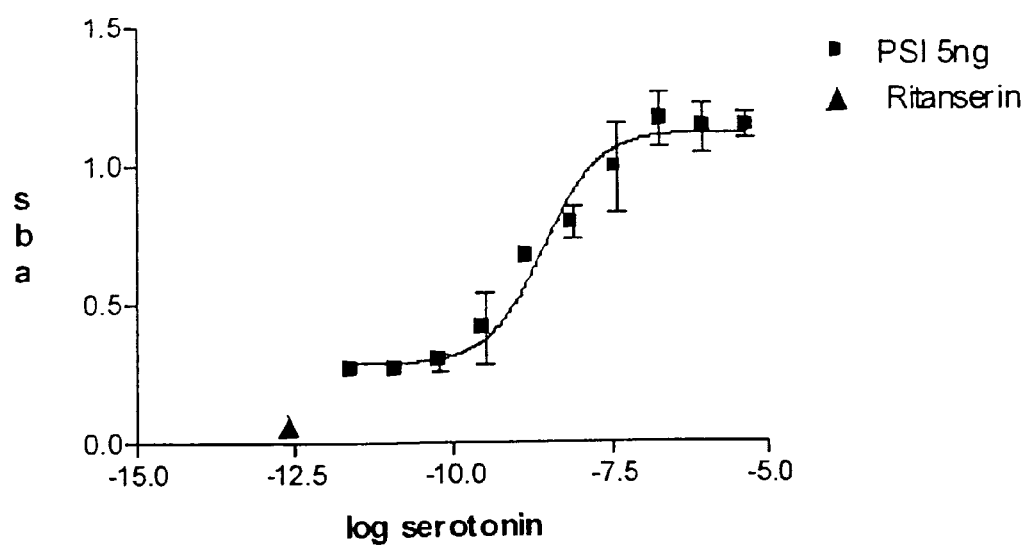

Figure 2. Inverse Agonist Pharmacology of Ritanserin at 5HT2A Receptors
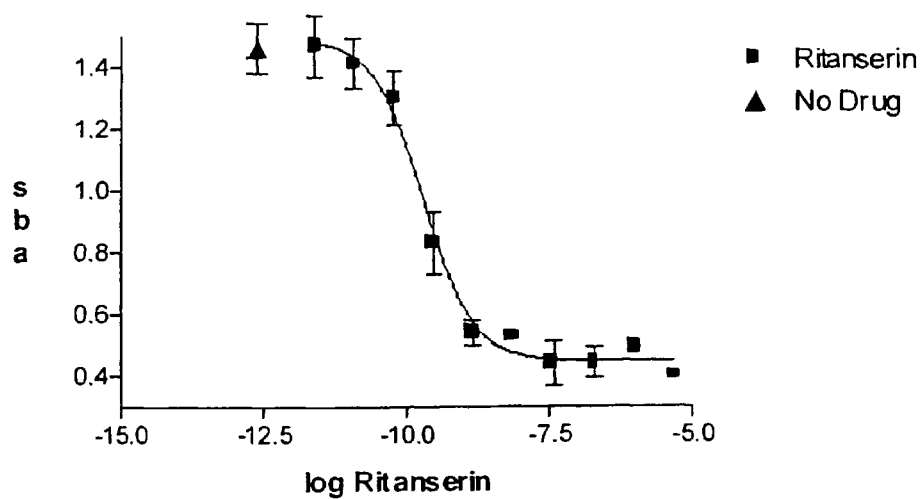

Figure 3. 5HT2A Inverse Agonist Curves for Typical and Atypical Antipsychotics
A) Typical Antipsychotic Haloperidol
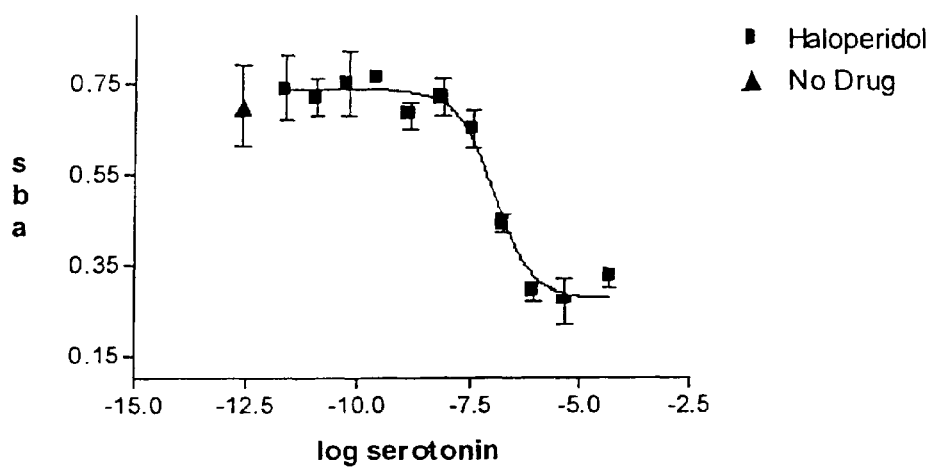
B) Atypical Antipsychotic Respiridone
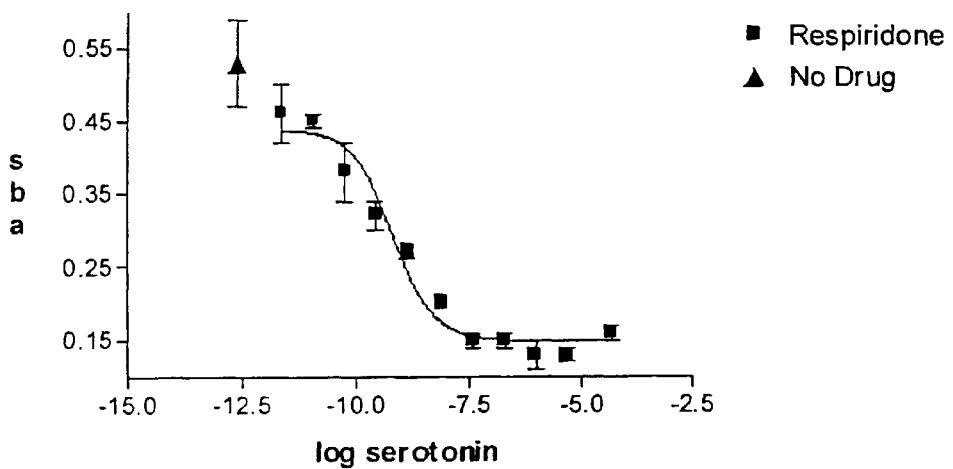

Figure 4. Structures of Compounds Discovered by 5HT2A Receptor Inverse Agonist Screening
"Haloperidol Like"
AC121394
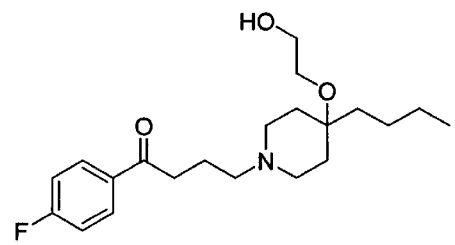
"Tricyclic Like"
AC116399
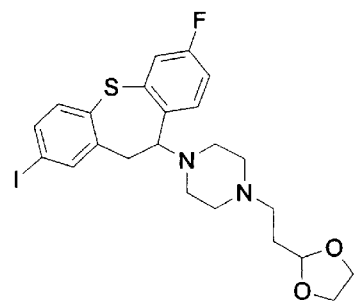

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: PCR Primer

<400> SEQUENCE: 1
agctccggga gaacagcatg ta                                    22

<210> SEQ ID NO 2
<211> LENGTH: 33
<212> TYPE: DNA
<213> ORGANISM: Artificial Sequence
<220> FEATURE:
<223> OTHER INFORMATION: PCR Primer

<400> SEQUENCE: 2

-continued

```
gagtgtggat ccatcaaggt gaatggtgag cag                                33

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
caatgaacag catagcagca a                                             21

<210> SEQ ID NO 4
<211> LENGTH: 34
<212> TYPE: DNA
<213> ORGANISM: Artificial Sequence
<220> FEATURE:
<223> OTHER INFORMATION: PCR Primer

<400> SEQUENCE: 4
ggtttcctct agaaaataga agttaattta gatt                               34
```

METHODS OF IDENTIFYING INVERSE AGONISTS OF THE SEROTONIN 2A RECEPTOR

This application claims the benefit of now abandoned U.S. Provisional Application Ser. No. 60/103,317 filed Oct. 7, 1998.

FIELD OF THE INVENTION

The present invention relates to methods of identifying compounds which act as inverse agonists of the serotonin (5-HT) 2A receptor, methods of screening individuals having disorders putatively associated with constitutively active 5-HT2A receptors, diagnostic test kits and methods of treatment for such individuals, methods of decreasing basal activity levels of the 5-HT2A receptor, and uses of inverse agonists as therapeutic agents for schizophrenia and psychosis.

BACKGROUND OF THE INVENTION

Schizophrenia is a devastating neuropsychiatric disorder that affects approximately 1% of the human population. It is characterized by a constellation of symptoms: "positive" symptoms such as hallucinations and delusions; and "negative" symptoms such as social and emotional withdrawal, apathy, and poverty of speech. The disorder usually develops early in life and is characterized by a chronic, often relapsing remitting course. Although the pathophysiology of this clinically heterogeneous disorder is unknown, genetic factors play a significant role. It has been estimated that the total financial cost for the diagnosis, treatment, and lost societal productivity of individuals affected by this disease exceeds 2% of the gross national product (GNP) of the United States. To date, there exist no definitive diagnostic tests for this disorder. Current treatment options available to psychiatrists primarily involve pharmacotherapy with a class of drugs known as antipsychotics. Antipsychotics are effective in ameliorating positive symptomotology, yet they frequently do not improve negative symptoms, and significant, treatment-limiting side effects are common.

Drugs that possess antipsychotic properties have been in clinical use since the early 1950's. The first compound shown to possess this property was chlorpromazine, and many of the subsequent compounds were derived from this phenothiazine antipsychotic. Currently, nine major classes of antipsychotics have been developed and are widely prescribed to treat psychotic symptoms irrespective of their etiology. Clinical use of these compounds are limited, however, by their side effect profiles. Nearly all of the "typical" or older generation compounds have significant adverse effects on human motor function. These "extrapyramidal" side effects, so termed due to their effects on modulatory human motor systems, can be both acute and chronic in nature. Acute effects include dystonic reactions, and a potentially life threatening but rare symptom constellation, neuroleptic malignant syndrome. Chronic side effects include akathisias, tremors, and tardive dyskinesia, a movement disorder characterized by involuntary writhing movements of the tongue and oral musculature seen with long-term administration of these agents. Due in large part to these disabling side effects, drug development in this class of compounds has been focused on newer "atypical" agents free of these adverse effects.

Various hypotheses have been proposed concerning the pathophysiology of schizophrenia, including genetic, environmental, and developmentally based theories. Current neuropharmacological theories are based, in large part, on the observation that antipsychotic drugs can improve the symptoms of schizophrenia, coupled with our current knowledge as to the mechanism of action of this class of drugs. Antipsychotic drugs have been shown, by both in vitro and in vivo methods, to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes.

The prevailing theory as to the mechanism of action of antipsychotic drugs involves antagonism of dopamine D2 receptors. This is based on the observation that these drugs have high affinity for this receptor in vitro, and that a correlation exists between their potency to block D2 receptors and their clinical efficacy. Unfortunately, it is likely that antagonism of dopamine D2 receptors also mediates the disabling extrapyramidal side effects. Interestingly, some antipsychotic drugs have been shown not to possess high affinity for D2 receptors, and therefore an alternate mechanism must be responsible for their clinical effects. The only other consistent receptor interaction that these drugs as a class display is antagonism of 5-HT2A receptors, suggesting that antagonism of these receptors is an alternate molecular mechanism that confers antipsychotic efficacy.

The observation that many of these drugs are antagonists of 5-HT2A receptors has led investigators to postulate that schizophrenia might be caused by heightened or exagerrated signal transduction through serotonergic systems. This theory is bolstered by a number of basic scientific and clinical observations regarding serotonergic systems and the 5-HT2A receptor in particular. Firstly, in addition to the known antipsychotics in widespread clinical usage, research compounds (e.g. ritanserin) that selectively block 5-HT2A receptors (with respect to D2 receptors) have also been shown to possess antipsychotic activity. Secondly, the 5-HT2A receptor mRNA and protein have been shown to be expressed in neural systems that mediate higher cognitive and affective functions, including the cerebral cortex, hippocampus, and amygdala. Thirdly, some of the positive symptoms that characterize the disease can be mimicked in normal individuals by the ingestion of the hallucinogenic indolamine lysergic acid diethylamide (LSD). It is known that LSD and similar hallucinogens exert their psychogenic effects, in part, through the activation of 5-HT2A receptors. G-protein coupled neurotransmitter receptors (GPCR's), including the 5-HT2A receptor, function as transducers of intercellular communication. Traditionally, these receptors have been assumed to exist in a quiescent state unless activated by the binding of an agonist (a drug that activates a receptor). When activated, receptors interact with G-proteins, resulting in the generation, or inhibition of, second messenger molecules such as cyclic AMP, inositol phosphates, and diacylglycerol. These second messengers then modulate the function of a variety of intracellular enzymes, including kinases and ion channels, which ultimately determine neuronal excitability and neurotransmitter release.

Over the last few years some fundamental observations have been made relating to ways in which these receptor molecules function. One of the most important of these has been the identification and characterization of constitutively active receptors. It is now appreciated that many, if not most, of the GPCR monoamine receptors can exist in a partially activated state in the absence of their agonists. This increased basal activity can be inhibited by a class of drugs aptly named inverse agonists, in that they function as the inverse of agonists. Inverse agonists differ mechanistically from classic (or neutral) antagonists. Antagonists compete against agonists and inverse agonists for access to the receptor, but do not possess the intrinsic ability to inhibit elevated basal or constitutive receptor responses.

Multiple lines of experimental evidence support the hypothesis that constitutively active neurotransmitter receptors may exist in the central nervous system and be causative for human neuropsychiatric disease. Constitutive activity has been observed with neurotransmitter receptors mutated in vitro. For instance, S. Cottechia et al. (*Proc. Natl. Acad. Sci. USA* 87, 1990, pp. 2896–2900) made constitutively active chimeric α-1 adrenergic receptor by replacing the third intracytoplasmic loop of the receptor with that of the β-2 adrenergic receptor. Also, P. Samama et al. (*J. Biol. Chem.* 268, 1993, pp. 4625–4636) generated a constitutively active β2 receptor by replacing four amino acid residues in the C-terminal region of the third intracytoplasmic loop with analogous residues from the α-1B receptor. Point mutations have been introduced into the muscarinic m5 receptor by random saturation mutagenesis (E. S. Burstein et al., *Biochem. Pharmacol.* 51, 1996, pp. 539–544; T. A. Spalding et al., *J. Pharm. Exp. Ther.* 275, 1995, pp. 1274–1279), resulting in more than 40 mutants that exhibit varying degrees of constitutive activity. The relative ease with which these receptors may be mutated to a constitutively active form suggests that constitutively active receptors may occur spontaneously in nature with a high frequency.

A strong argument for the potential contribution of constitutively active receptors to human neuropsychiatric disease would be the finding that similar mutations are causative in other human diseases. Mutations in the G-protein coupled receptor gene family are common and are increasingly recognized to cause a number of human diseases. Most of these mutations are single nucleotide or point mutations that alter the structure and function of the receptor molecules. For instance, point mutations in the receptors rhodopsin and vasopressin (J. Nathans, *Cell* 78, 1994, pp. 357–360; W. Rosenthal et al., *Nature* 359, 1992, pp. 233–235) cause reading frame shifts, prematurely terminating translation of these proteins, resulting in non-functioning receptors that subsequently cause color blindness and nephrogenic diabetes insipidus, respectively. Robinson and colleagues (P. R. Robinson et al., *Neuron* 9, 1992, pp. 719–725) characterized the first mutation in a human G-protein coupled receptor that resulted in constitutive activation of the receptor and caused human disease. They found that when the amino acid Lys296 was mutated to Glu in the visual pigment rhodopsin, it was able to activate the G-protein transducin in the absence of light (its natural "agonist"). This particular mutation causes a particularly severe phenotype of retinitis pigmentosa (T. J. Keen et al., *Genomics* 11, 1991, pp. 199–205).

The number of constitutively active receptors that cause human disease is expanding. Multiple endocrinological and oncological disorders are caused by mutations that give rise to constitutively active receptors. These mutations have been shown to occur as a result of both spontaneous somatic events and as inherited germ line defects. A single point mutation in the luteinizing hormone receptor (Asp578-Gly), which causes male-linked precocious puberty, has been shown to be familial in caucasian populations (A. Shenker et al., *Nature* 365, 1993, pp. 652–654) and sporadic in Japanese populations (K. Yano et al., *J. Clin. Endocrin. Metab.* 79, 1994, pp. 1818–1823). Two different point mutations in the parathyroid hormone receptor confer constitutive activity and cause Jansen's metaphyseal chondroplasia (E. Schipani et al., *New Eng. J. Med.* 335, 1996, pp. 708–714; E. Schipani et al., *Science* 268, 1995, pp. 98–100). Furthermore, two activating mutations were found in the thyrotropin receptor, both of which were found to cause many sporadic thyroid adenomas (J. Parma et al., *Nature* 365, 1993, pp. 649–651). Taken together, these data attest to the widespread biological significance of constitutively active receptors and their role in human disease. It is, therefore, highly likely that constitutively active G-protein coupled receptors exist in the human nervous system and mutations in these neurotransmitter receptors, including the 5-HT2A receptor, may cause human neuropsychiatric disease.

Constitutive activity has been described for a growing number of G-protein coupled neurotransmitter receptors. The dopamine D2 receptor has been reported to be constitutively active, and some antipsychotic compounds have been described as inverse agonists, although many of these compounds appear to be classical antagonists (Nilsson, C. L., et al., *Neuropsychopharmacology* 15, 1996, pp. 53–61; Hall, D. A. and Strange, P. G., *Brit. J Pharm.*, 121, 1997, pp. 731–736) Similarly, of the thirteen known serotonin receptor subtypes, only three have been shown to possess constitutive activity, the 5-HT1A, 5-HT1D and 5-HT2C receptors. For example, E. L. Barker et al. (*J. Biol. Chem.* 269, 1994, pp. 11687–11690) describe an in vitro assay in which the wild-type 5-HT2C receptor displays constitutive activity. They further report that certain classically defined antagonists of the receptor, actually act as inverse agonists.

The creation of an activated 5-HT2A receptor by mutagenesis was recently described (Egan, C., T., et., al., *J. Pharm Exp. Ther.* 286(1), 1998, pp. 85–90). Altering amino acid 322 from the wild type cysteine to lysine, glutamate, or arginine created activated 5-HT2A receptor mutants. This amino acid was chosen because it is analogous to the activating mutation produced in the α1b receptor (Kjelsberg, M. A., et al., *J. Biol. Chem.* 267(3), 1992, pp. 1430–1433). The activated 5-HT2A receptor displayed measurable constitutive activity, and six antipsychotics were shown to be inverse agonists (Egan, C. T., ibid.; and Egan, C. T., et al., *Annals N.Y. Acad. Sci.*, 1999, pp. 136–139). These authors were unable to measure the constitutive activity of the wild type receptor in their assay, and an insufficient number of clinically relevant compounds comprising the various chemical classes of antipsychotics were tested. This precluded the authors from recognizing the significance of 5-HT2A receptor inverse agonism and efficacy as an antipsychotic.

SUMMARY OF THE INVENTION

Since 5-HT2A receptors may be critical mediators of antipsychotic drug activity, and as the exact nature of this interaction (antagonism vs. inverse agonism) is poorly understood, many antipsychotic compounds have been tested for their functional activity at this receptor. It has surprisingly been found that the 5-HT2A receptor is constitutively active in the assay described in the present specification, and that nearly all antipsychotic drugs are inverse agonists of this receptor. The striking correlation between antipsychotic efficacy and inverse agonism of the 5-HT2A receptor argues that inverse agonism of this receptor is a fundamental molecular mechanism of action of this class of drugs. This observation has practical applications in the development of novel antipsychotic agents with more favorable side effect profiles as well as potentially broader efficacy against the negative symptomotology of psychotic disorders. This finding also has important implications for the pathophysiology, diagnosis and management of schizophrenia and related psychoses.

Accordingly, the present invention relates in one aspect to a method of identifying a compound which acts as an inverse agonist of the 5-HT2A receptor, the method comprising contacting a constitutively active 5-HT2A receptor with at least one test compound and determining any decrease in the level of basal activity of the 5-HT2A receptor so as to identify a test compound which is an inverse agonist of the 5-HT2A receptor. In a related aspect, this method is used to identify compounds useful in the treatment of schizophrenia or psychosis.

In another aspect, the invention relates to a method of identifying a mutation in the 5-HT2A receptor gene, the mutation being suspected of conferring constitutive activity on the receptor, the method comprising:

(a) extracting nucleic acid from a biological sample obtained from an individual having a disorder or condition putatively associated with constitutive activity of the 5-HT2A receptor;

(b) preparing cDNA from the extracted nucleic acid;

(c) selecting from the cDNA in step (b) cDNA encoding the 5-HT2A receptor;

(d) transfecting a cell with an expression vector comprising said selected cDNA;

(e) selecting a cell expressing constitutively active 5-HT2A receptor; and (f) sequencing the cDNA in said selected cell to detect the mutation(s).

In a further aspect, the invention relates to a method of diagnosing a disorder or condition, or a susceptibility to a disorder or condition, associated with constitutive activity of the 5-HT2A receptor, the method comprising:

(a) obtaining a biological sample from an individual putatively affected by or susceptible to a disorder or condition associated with constitutive activity of the 5-HT2A receptor;

(b) isolating from said biological sample a nucleic acid sequence encoding said receptor, or a portion of said nucleic acid sequence corresponding to the portion of the gene identified to include mutation(s) by the mutation identification method described above; and (c) detecting the presence or absence of the mutation(s) in said nucleic acid sequence or said portion thereof.

The presence of one or more mutations in the nucleic acid sequence may, for example, be detected by sequencing the nucleic acid sequence and comparing it with a sequence known or previously identified to contain mutation(s).

In another aspect, the present invention relates to a test kit for detecting mutation(s) in the gene encoding the 5-HT2A receptor, said mutations giving rise to constitutive activity of the 5-HT2A receptor, the test kit comprising a nucleic acid sequence corresponding to a portion of the gene identified by the mutation identification method described above to include at least one mutation.

Furthermore, the present invention relates to a method of decreasing the basal activity level of the 5-HT2A receptor in a subject in need thereof, the method comprising contacting a 5-HT2A receptor in said subject with an inverse agonist of the 5-HT2A receptor in an amount effective to substantially decrease the level of basal activity of said receptor. In a preferred embodiment, the inverse agonist is selective for the 5-HT2A receptor (i.e., has at least about ten times greater affinity for the 5-HT2A receptor than for at least one other neurotransmitter receptor). In another preferred embodiment, the inverse agonist of the 5-HT2A receptor has little or substantially no anti-dopaminergic activity. In a related aspect, the invention relates to a method of decreasing serotonergic neurotransmission through the 5-HT2A receptor, the method comprising contacting a 5-HT2A receptor with an inverse agonist of the 5-HT2A receptor in an amount effective to substantially decrease the level of basal activity of said receptor.

In another aspect, the present invention relates to a method of ameliorating symptoms of schizophrenia or psychosis in a subject in need thereof, the method comprising administering to the subject a therapeutically effective amount of an inverse agonist of the 5-HT2A receptor.

In yet other aspects, the invention relates to use of an inverse agonist of the 5-HT2A receptor for the preparation of a medicament for substantially decreasing the basal activity level of a constitutively active 5-HT2A receptor. Preferably, in this use, the inverse 5-HT2A agonist is selective for the 5-HT2A receptor. In another embodiment relating to such use, the inverse agonist of the 5-HT2A receptor has little or substantially no anti-dopaminergic activity. The invention also relates in certain aspects to use of a 5-HT2A receptor to identify compounds acting as inverse agonists at said receptor, as well as use of a 5-HT2A receptor to identify a compound acting as an inverse agonist at said receptor and useful in the treatment of schizophrenia or psychosis.

The present disclosure represents the first reported measurement of the constitutive activity of the wild type (non-mutated) human 5-HT2A receptor and correlation of the molecular property of inverse agonism at this receptor with antipsychotic efficacy. Since most mutations in GPCR's have been shown to alter their binding and coupling characteristics, the ability to measure intrinsic activity at the wild type receptor, and to use this receptor in assay for drug discovery is critical.

Inverse agonists of the 5-HT2A receptor, as identified by the present methods, may be used to alleviate or treat disorders or conditions associated with constitutive activity of the 5-HT2A receptor. It is anticipated that compounds that are inverse agonists of the 5-HT2A receptor will be less likely to cause extrapyramidal side effects than many of the typical antipsychotics in current use. In particular, compounds that are selective for the 5-HT2A receptor, in that they exhibit little or no anti-dopaminergic activity, are expected to have fewer extrapyramidal side effects. Furthermore, inverse agonists may be useful in the alleviation or treatment of the negative symptoms of schizophrenia. This is supported by the fact that some of the "atypical" antipsychotics, which are described herein to act as inverse agonists at the 5-HT2A receptor, have been reported to have beneficial effects on negative symptoms.

Definitions

A "test compound" is intended to include any drug, compound or molecule with potential biological activity.

"Constitutive activity" is defined as the elevated basal activity of a receptor which is independent of the presence of an agonist. Constitutive activity of a receptor may be measured using a number of different methods, including cellular (e.g., membrane) preparations (see, e.g., A. J. Barr and D. R. Manning, *J. Biol. Chem.* 272, 1997, pp. 32979–32987), purified reconstituted receptors with or without the associated G-protein in phospholipid vesicles (R. A. Cerione et al., *Biochemistry* 23, 1984, pp. 4519–4525), and functional cellular assays (described herein).

An "inverse agonist" is defined as a compound which decreases the basal activity of a receptor (i.e., signal transduction mediated by the receptor). Such compounds are also known as negative antagonists.

An "antagonist" is defined as a compound which competes with an agonist or inverse agonist for binding to a receptor, thereby blocking the action of an agonist or inverse agonist on the receptor. However, an antagonist (also known as a "neutral" antagonist) has no effect on constitutive receptor activity.

The "5-HT2A receptor" is defined as the human serotonin receptor subtype characterized through molecular cloning and pharmacology as detailed in Saltzman, A G., et al., *Biochem. Biophys. Res. Comm.* 181(3), pp. 1469–1478; and Julius, D., et al., *Proc. Natl. Acad. Sci.* 87, pp. 928–932.

"Transfection" is defined as any method by which a foreign gene is inserted into a cultured cell.

A "biological sample" indicates a sample of tissue or body fluid obtained from a subject. Biological samples relevant to obtaining 5-HT2A receptors include, but are not limited to, blood, serum (5-HT2A receptors being present in platelets) and/or brain tissue, within which the receptor genes are known to be expressed in identical forms.

The term "subject" refers to an animal, preferably a mammal, most preferably a human, who is the object of treatment, observation or experiment.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated.

The terms "selectivity" or "selective," when used in the context of inverse agonists of 5-HT2A, are used to indicate compounds having at least approximately 10-fold higher affinity for the 5-HT2A receptor subtype than towards at least one, and preferably more than one, other neurotransmitter receptor.

EC50 for an agonist is intended to denote the concentration of a compound needed to achieve 50% of a maximal response seen in R-SAT. For inverse agonists, EC50 is intended to denote the concentration of a compound needed to achieve 50% inhibition of an R-SAT response from basal, no compound, levels.

BRIEF DESCRIPTION OF THE DRAWINGS

FIG. 1 shows the dose response relationship for serotonin at the 5-HT2A receptor as observed in R-SAT assays. Responses are plotted as the change in absorbance measured at 420 nm. Ten serial 1:5 dilutions of serotonin starting from 5 $\mu$M were tested. The squares depict the response of the 5-HT2A using the PSI® expression vector at a DNA concentration of 5 ng per well. The triangle depicts the response to 1 $\mu$M ritanserin. Data are from duplicate determinations at each drug concentration, where the error bars denote the standard error of the mean. The EC50 for serotonin is 7 nM. Note the elevated basal activity of this receptor as documented by the inhibition below baseline seen with the inverse agonist ritanserin.

FIG. 2 shows the dose response relationship at the 5-HT2A receptor for the inverse agonist ritanserin as determined using R-SAT analysis. Responses are plotted as the change in absorbance measured at 420 nm. Ten serial 1:5 dilutions of drug starting from 5 $\mu$M were tested. The squares depict the data obtained for ritanserin, while the triangle denotes the basal, no drug, response. Data are from duplicate determinations at each drug concentration, where the error bars denote the standard error of the mean. The EC50 for ritanserin is 140 pM. Ritanserin displays high affinity negative intrinsic activity at the 5-HT2A receptor.

FIG. 3 shows the dose response relationship for two representative antipsychotics as inverse agonists of the 5-HT2A receptor as determined by R-SAT analysis. Responses are plotted as the change in absorbance measured at 420 nm. Ten serial 1:5 dilutions of drug starting from 5 $\mu$M were tested. The squares depict the data obtained for haloperidol in (A), and risperidone in (B), while the triangles denote the basal, no drug, response. Data are from duplicate determinations at each drug concentration, where the error bars denote the standard error of the mean. The EC50 values are 120 nM for haloperidol and 1 $\mu$M for risperidone, respectively.

FIG. 4 shows the chemical structures of two representative compounds identified as inverse agonists of the 5-HT2A receptor using the screening methods of the present invention. Compound AC121394, which is haloperidol-like, and compound AC116399, which is tricyclic-like, were identified out of a library comprising 135,000 structurally diverse organic compounds.

DETAILED DESCRIPTION OF THE INVENTION

In one embodiment, a method of identifying a compound which acts as an inverse agonist of the 5-HT2A receptor comprises contacting a constitutively active 5-HT2A receptor with at least one test compound and determining any decrease in the level of basal activity of the 5-HT2A receptor so as to identify the test compound(s) which act as inverse agonists of the 5-HT2A receptor. This method may be used to identify compounds useful in the treatment of schizophrenia or psychosis.

In a preferred embodiment, a method of identifying a compound which acts as an inverse agonist of the serotonin 5-HT2A receptor comprises:

(a) culturing cells which express a constitutively active 5-HT2A receptor;

(b) incubating the cells with at least one test compound; and (c) determining any decrease in basal activity level of the 5-HT2A receptor so as to identify a test compound which is an inverse agonist of the 5-HT2A receptor.

Where a mutation in the gene encoding the 5-HT2A receptor is suspected of conferring constitutive activity on the receptor, a method of identifying a mutation in the 5-HT2A receptor gene comprises:

(a) extracting nucleic acid from a biological sample obtained from an individual having a disorder or condition putatively associated with constitutive activity of the 5-HT2A receptor;

(b) preparing cDNA from the extracted nucleic acid;

(c) selecting from the cDNA in step (b) cDNA encoding the 5-HT2A receptor;

(d) transfecting a cell with an expression vector comprising said selected cDNA;

(e) selecting a cell expressing constitutively active 5-HT2A receptor; and (f) sequencing the cDNA in said selected cell to detect the mutation(s).

The extracted nucleic acid is preferably RNA, from which cDNA may be prepared by reverse transcription. The cDNA which encodes the 5-HT2A receptor is preferably amplified using oligodeoxynucleotide probes specific to the 5-HT2A receptor gene (i.e., based on the known sequence of the gene).

The present invention also provides a method of diagnosing a disorder or condition, or a susceptibility to a disorder or condition, associated with constitutive activity of the 5-HT2A receptor. This method comprises:

(a) obtaining a biological sample from an individual putatively affected by or susceptible to a disorder or condition associated with constitutive activity of the 5-HT2A receptor;

(b) isolating from said biological sample a nucleic acid sequence encoding said receptor, or a portion of said nucleic acid sequence corresponding to the portion of the gene identified to include mutation(s) by the mutation identification method described above; and (c) detecting the presence or absence of the mutation(s) in said nucleic acid sequence or said portion thereof.

The presence of such mutations in the nucleic acid sequence may, for example, be detected by sequencing the nucleic acid sequence and comparing it with a sequence known or previously identified to contain mutation(s).

The present invention also provides a test kit for detecting mutation(s) in the gene encoding the 5-HT2A receptor, wherein the mutations give rise to constitutive activity of the 5-HT2A receptor. The test kit comprises a nucleic acid sequence corresponding to a portion of the gene identified by the mutation identification method described above to include at least one mutation.

The present invention also provides a method of decreasing the basal activity level of the 5-HT2A receptor in a subject in need thereof. This method comprises contacting a 5-HT2A receptor in said subject with an inverse agonist of the 5-HT2A receptor in an amount effective to substantially decrease the level of basal activity of said receptor. In a preferred embodiment, the inverse agonist is selective for the 5-HT2A receptor. In another preferred embodiment, the inverse agonist of the 5-HT2A receptor has little or substantially no anti-doparninergic activity.

Transfection of cells in the present invention may be performed according to any of numerous methods known in the art. In general, DNA sequences encoding the 5-HT2A receptor may be inserted into suitable cloning vectors which may conveniently be subjected to recombinant DNA procedures. These vectors may be autonomously replicating, i.e., vectors which exist as extrachromosomal entities, the replication of which are independent of chromosomal replication (e.g., plasmids). Alternatively, these vectors may be ones which, when introduced into a host cell, are integrated into the host cell genome and replicate together with the chromosome(s) into which they have been integrated.

The DNA sequences encoding the 5-HT2A receptor may suitably be derived from sample genomic DNA, or cDNA that has been reverse transcribed from sample RNA, in accordance with well-established molecular biological techniques (e.g., as described in Sambrook et al., *Molecular Cloning: A Laboratory Manual,* 2nd Ed., Cold Spring Harbor Laboratory, Cold Spring Harbor, N.Y., 1989).

When transfected, the DNA sequence encoding the 5-HT2A receptor should be operably connected to a suitable promoter sequence. The promoter may be any DNA sequence which shows transcriptional activity in the host cell of choice and may be derived from genes encoding proteins either homologous or heterologous to the host cell. An example of a suitable promoter is the SV40 promoter (Subramani et al., *Mol. Cell Biol.* 1, 1981, pp. 854–864).

The DNA sequence encoding the 5-HT2A receptor may also be operably connected to a suitable terminator, such as the human growth hormone terminator (Palmiter et al.). The vector may further comprise elements such as polyadenylation signals (e.g., from SV40 or the adenovirus 5 Elb region), transcriptional enhancer sequences (e.g., the SV40 enhancer) and translational enhancer sequences (e.g., those encoding adenovirus VA RNAs).

The vector may further comprise a DNA sequence enabling the vector to replicate in the host cell in question. An example of such a sequence (when the host cell is a mammalian cell) is the SV40 origin of replication.

The procedures used to ligate the DNA sequences encoding the 5-HT2A receptor, the promoter and the terminator, respectively, and the procedures used to insert them into suitable vectors containing the information necessary for replication, are well known to persons skilled in the art (see, e.g., Sambrook et al., supra).

Cells which may be used in the present method include any cells capable of mediating signal transduction via the 5-HT2A receptor, either via endogenous expression of this receptor (e.g., certain types of neuronal cells lines that natively express the 5-HT2A receptor), or following transfection of cells with plasmids containing the 5-HT2A receptor gene. Such cells are typically mammalian cells (or other eukaryotic cells, such as insect cells or Xenopus oocytes), because cells of lower life forms generally lack the appropriate signal transduction pathways for the present purpose. Examples of suitable cells include: the mouse fibroblast cell line NIH 3T3 (ATCC CRL 1658), which responds to transfected 5-HT2A receptors by stimulating growth (described herein); RAT 1 cells (Pace et al., *Proc. Natl. Acad. Sci. USA* 88, 1991, pp. 7031–7035); and pituitary cells (Vallar et al., *Nature* 330, 1987, pp. 556–558). Other useful mammalian cells for the present method include HEK 293 cells, CHO cells and COS cells.

Methods of transfecting mammalian cells and expressing DNA sequences introduced in the cells are described in, e.g., Kaufnan and Sharp, *J. Mol. Biol.* 159 1982, pp. 601–621; Southern and Berg, *J. Mol. Appl. Genet.* 1, 1982, pp. 327–341; Loyter et al., *Proc. Natl. Acad. Sci. USA* 79, 1982, pp. 422–426; Wigler et al., *Cell* 14, 1978, p. 725; Corsaro and Pearson, *Somatic Cell Genetics* 7, 1981, p. 603; Graham and van der Eb, *Virology* 52, 1973, p. 456; Neumann et al., *EMBO J.* 1, 1982, pp. 841–845; and Wigler et al., *Cell* 11, 1977, pp. 223–232.

The screening assay used in the present method may include any functional assay that would reflect 5-HT2A receptor activity in, for instance, membrane preparations or living cells, mammalian and non-mammalian, in response to a ligand (agonist, antagonist and, inverse agonists) and, in particular, an assay suited for detecting constitutive activity of receptors. Examples of suitable assay systems include those using insect cells (such as cells of *Spodoptera frugiperda,* Sf9, transfected with baculoviris vector carrying the receptor gene (e.g., as described in A. J. Barr and D. R. Manning, *J. Biol. Chem.* 272, 1997, pp. 32979–32987; J. L. Hartman and J. K. Northup, *J. Biol. Chem.* 271, 1996, pp. 22591–22597; J. Labrecque et al., *Mol. Pharmacol.* 48, 1995, pp. 150–159)), or Xenopus oocytes expressing cloned receptors (e.g., as described in Y. G. Ni and R. Miledi, *Proc. Natl. Acad. Sci. USA* 94, 1997, pp. 2036–2040), or HEK293 cells transiently expressing cloned receptors (e.g., as described in M. Tiberi and M. Caron, *J. Biol. Chem.* 269, 1994, pp. 27925–27931), or CHO cells (e.g., as described in A. Newman-Tancredi et al., *Neuropsychopharmacology* 18, 1998, pp. 396–398). A preferred assay is the Receptor Selection and Amplification Technology (R-SAT) assay disclosed in U.S. Pat. No. 5,707,798, the disclosure of which is hereby incorporated by reference in its entirety.

Although the constitutive activity of the 5-HT2A receptor may, in certain assays, be detected in itself, it may be more suitable in other instances to overexpress the receptor to augment basal signaling and improve the sensitivity of detection of inverse agonism. Over-expressiona of receptors in cultured cells, as well as transgenic animals, has been shown to result in increased constitutive activity of the receptor (G. Milligan et al., *TIPS* 16, pp. 10–13; S. A. Akhter et al. *J. Biol. Chem.* 272(34), pp. 21253–21259). Overexpression may be experimentally accomplished by using an excess of plasmid DNA encoding receptors when transfecting cells as part of functional assays of cloned monoamine receptor subtypes. The excess of DNA may vary from one assay to the next but may, in the currently preferred assay, be approximately 10-fold in excess of that required to provide measurable signaling.

Attempts have been made to link neurotransmitter receptors to neuropsychiatric diseases, primarily by identifying polymorphisms in the receptor genes by methods including restriction fragment length polymorphism (RFLP), single strand conformational polymorphism (SSCP) and multipoint, parametric and non-parametric methods of linkage analysis. For example, the various dopamine receptors have been shown to possess multiple polymorphic variants in the human population (H. H. M. Van Tol et al., *Nature* 342, 1992, pp. 149–152; N. Craddock et al., *Psychiat. Genet.* 5, 1989, pp. 63–65). However, attempts at associating those polymorphisms with neuropsychiatric disease are unlikely to succeed because there is no credible evidence that the polymorphisms have functional significance. Therefore, the present method of identifying mutant receptors represents a substantial advantage in that it identifies only functionally altered mutants. These phenotypically distinct receptors are much more likely to be related to human disease.

Thus, the present diagnostic methods are amenable to screening human populations for mutant 5-HT2A receptor genes that create a constitutively active phenotype. As the human 5-HT2A receptor gene contains introns (A. G. Saltzman et al., supra), amplification of receptor DNA will typically be carried out by reverse transcriptase-based PCR (RT-PCR; e.g., as described in Elion, E. A., *Current Protocols in Molecular Biology*, 1998; F. M. Ausebel et al., *EDS*, pp. 3.17.1–3.17.10). This method creates a representative cDNA pool from an individual's RNA that is extracted from suitable samples (e.g., serum or brain tissue) and amplifies the receptor gene using oligonucleotide probes based on the known sequence of the gene. The resulting PCR products are then subcloned into mammalian expression vectors, and competent bacteria such as *E. coli* are subsequently transformed. Bacterial cultures are inoculated during transformation, thereby ensuring that the DNA isolated from this culture represents a mixture of plasmids that contains copies of both alleles of the amplified 5-HT2A receptor gene. Phenotypic cellular assays (including R-SAT), select for only those cells transfected with plasmids that encode functional receptors, as only these cells will transduce mitogenic signals and continue to grow. If the transfected receptor cDNA harbors a mutation that confers a constitutively active phenotype, this is detectable by the presence of higher levels of basal receptor activity measured in the assay and verified by incubation of these transfected cells with a known inverse agonist (e.g. as described in the Example below).

After a constitutively active 5-HT2A receptor has been identified in the assay, a formal characterization of the mutation responsible for this phenotype is carried out. For example, an aliquot of the original ligation reaction from all patients in whom a constitutively active receptor has been identified by screening is used to re-transform competent bacteria, and individual clones are selected. The individual clones are then grown in larger quantities and plasmid DNA is extracted according to any of various methods known in the art. Restriction enzyme digestions will identify 5-HT2A gene-containing constructs, and a number of these are then subjected to automated DNA sequencing.

Mutant 5-HT2A receptors, identified by the present method, may be included in a test kit for detecting mutation (s) in the gene encoding the 5-HT2A receptor. Such a test kit may conveniently comprise a nucleic acid sequence corresponding to a portion of the gene encoding the 5-HT2A receptor comprising at least one mutation identified by the present method to give rise to constitutive activity of the receptor.

A suitable in vivo experimental system for validation of both the physiological role of constitutively active 5-HT2A receptors, and the effects of selective 5-HT2A inverse agonists as therapeutic agents, is a transgenic animal model in which constitutive signaling through the 5-HT2A receptor has been achieved. Transgenic animals, preferably mice, may for instance be generated by two distinct approaches: 1) brain-specific over-expression of wild-type human 5-HT2A receptors; and 2) regulated expression of a constitutively active 5-HT2A receptor mutant. Both approaches rely upon standard molecular biological techniques known to those skilled in the art.

Briefly, the first approach involves subcloning of the wild type human 5-HT2A receptor gene into an appropriate transgenic vector, the expression of which is driven by a strong promoter (e.g., the CMV promoter). Brain-specific expression may be achieved by incorporating vector constructs comprising the human 5-HT2A receptor gene into the 5-HT2A genomic promoter region of the host animal by site-specific homologous recombination (K. Rajewsky et. al., *J. Clin. Invest.* 98(3), 1996, pp. 600–603). This is feasible, as both the human and mouse promoter regions for the 5-HT2A receptor gene have been cloned and characterized (Zhu, Q., Chen, K., and Shih, J. C., *J. Neuroscience* 15(7), 1995, pp. 4885–4895.). A transgenic animal may then be generated by injection of the vector construct into embryonic stem cells of the selected host animal (typically, a mouse) in accordance with standard procedures (M. R. Capecchi, *Trends Genet.* 5, 1989, pp. 70–76). This approach will result in regionally specific over-expression of the wild-type human 5-HT2A receptor in mouse brain.

The alternative approach requires the generation of a mutant human receptor which has a significantly higher basal activity than the wild-type gene. By applying standard PCR-based site-directed mutagenesis (e.g., as disclosed in E. S. Burstein et al., *Biochem. Pharmacol.* 51, 1996, pp. 539–544; and T. A. Spalding et al., *J. Pharm. Exp. Ther.* 275, 1995, pp. 1274–1279, for the muscarinic m5 receptor), it is possible to generate a receptor mutant that will exhibit increased constitutive activity. Using homologous recombination to incorporate a transgenic expression vector in which the mutant human gene is expressed from the native mouse promoter, without overexpression, would result in an animal with regional specific brain expression of an activated human 5-HT2A receptor mutant.

The present disclosure provides a series of human 5-HT2A receptor mutants that have increased constitutive activity compared to that observed in the wild type receptor, any of which are suitable for incorporation into a transgenic mouse model. Inverse agonists of the 5-HT2A receptor identified by the present methods may suitably be tested for activity in vivo in the transgenic mouse models described above, in which the effect of the compounds on locomotor activity, startle habituation and prepulse inhibition may conveniently be studied (T. A. Sipes and M. A. Geyer, *Neuropharmacology*, 33(3/4), pp. 441–448). Other animal models which may be used for this purpose include 5-HT agonist induced head twitches in mice or rats, substantially as disclosed by J. H. Kehne et al., supra, which may be reduced by administration of inverse agonists of the 5-HT2A receptor.

The present invention provides a method of ameliorating symptoms of schizophrenia or psychosis in a subject in need thereof, the method comprising administering to the subject a therapeutically effective amount of an inverse agonist of the 5-HT2A receptor.

Inverse agonists of the 5-HT2A receptor identified by the methods of the present invention may be formulated in pharmaceutical compositions comprising one or more inverse agonist compounds together with a pharmaceutically acceptable diluent or excipient. Such compositions may be formulated in an appropriate manner and in accordance with accepted practices such as those disclosed in *Remington's Pharmaceutical Sciences*, Gennaro, Ed., Mack Publishing Co., Easton Pa., 1990.

Particularly desirable inverse agonists of the 5-HT2A receptor will exhibit considerable selectivity for that receptor. Selectivity may, in the present context, be defined as an at least 10-fold higher affinity for the 5-HT2A receptor subtype than towards at least one, and preferably more than one, other neurotransmitter receptor tested. Examples of neurotransmitter receptors against which potentially selective inverse 5-HT2A agonists may suitably be tested include histamine, dopamine, muscarinic and adrenergic receptors, as well as the other existing serotonin receptor subtypes. 5-HT2A receptor inverse agonists may be effective in the treatment of a number of neuropsychiatric diseases and disorders such as psychosis or schizophrenia without the attendant undesirable extrapyramidal side effects previously observed with non-selective compounds, notably most classical antipsychotic drugs. It is currently believed that favorable therapeutic properties will be found in selective inverse 5-HT2A agonists that have little or substantially no anti-dopaminergic activity, in particular as antagonists of the dopamine D2 receptor, as such activity is assumed to give rise to many of these extrapyramidal side effects. To identify compounds that have the desired selectivity for 5-HT2A, the present assay method should also include cells expressing at least one other neurotransmitter receptor and preferably includes cells expressing a number of different neurotransmitter receptors.

Advantageously, inverse agonist compounds may be administered in a single daily dose, or the total daily dosage may be administered in divided doses two, three or four times daily. Furthermore, compounds of the present invention may be administered in intranasal form via topical use of suitable intranasal vehicles, or via transdermal routes using those forms of transdermal skin patches well known to persons skilled in the art.

The dosage regimen for 5-HT2A inverse agonist compounds will be selected in accordance with a variety of factors. These include type, species, age, weight, sex and medical condition of the patient; the severity of the condition to be treated; the route of administration; the renal and hepatic finction of the patient; and the particular compound employed. A physician of ordinary skill can readily determine and prescribe the effective amount of the drug required to prevent, counter or arrest the progress of the disease or disorder which is being treated.

The daily dosage may be varied over a wide range from about 0.01 to about 100 mg per adult human per day. An effective amount is ordinarily supplied at a dosage level of about 0.0001 mg/kg to about 25 mg/kg body weight per day. Preferably, the range is from about 0.001 to about 10 mg/kg of body weight per day, and especially from about 0.001 mg/kg to about 1 mg/kg of body weight per day. The compounds may be administered on a regimen of 1 to 4 times per day.

Inverse agonist compounds may be used alone at appropriate dosages defined by routine testing in order to obtain optimal pharmacological effect on the serotonin 5-HT2A receptor, while minimizing any potential toxic or otherwise unwanted effects. In addition, it is believed that 5-HT2A selective inverse agonists may be used as adjunctive therapy with known antipsychotic drugs to reduce the dosage required of these traditional drugs, and thereby reduce their extrapyramidal side effects.

The present invention is further disclosed in the following Example, which is not in any way intended to limit the scope of the invention as claimed.

EXAMPLE

The functional receptor assay, Receptor Selection and Amplification Technology (R-SAT), was used (essentially as disclosed in U.S. Pat. No. 5,707,798) to investigate the pharmacological phenotype of the 5-HT2A receptor. The 5-HT2A receptor gene was amplified by nested PCR from brain cDNA using the-following oligodeoxynucleotides based on published sequences: 5'#1: 5'-agctccgggagaacagcatgta-3' ; 5'#2:(SEQ ID NO1) 5'-gagtgtggatccatcaaggtgaatggtgagcag-3' (SEQ ID NO2); 3'#1: 5'-caatgaacagcatagcagcaa-3' (SEQ ID NO: 3); 3'#2: 5'-ggtttcctctagaaaatagaagttaatttagatt-3' (SEQ ID NO: 4) (Saltzman et. al., *Biochem. Biophys. Res. Comm.* 181(3), 1991, pp. 1469–1478).

The cDNA was obtained by reverse transcription of total RNA isolated from human brain tissue in accordance with standard techniques (see, Sambrook et al, supra). The human brain tissue was obtained from a 100-year old female free of neuropsychiatric disease. The PCR product was subdloned onto the TOPO PCR 2.1® vector (Invitrogen, Inc.) in accordance with the manufacturer's protocol. A Bam-H1 (blunted with T4 polymerase)-Not-1 DNA fragment containing the gene was subcloned into the mammalian expression vector PSI® (Promega, Inc.) for heterologous expression in R-SAT.

Varying doses of 5-HT2A receptor plasmid DNA were transfected into NIH 3T3 cells (at 70% confluence) using the transfection reagent Superfect® (Qiagen, Inc.). 5-HT2A receptor DNA transfection mixtures (per well of a 96-well cell culture dish) were composed of from 5 to 50 ng/well of receptor DNA, 25 ng/well of β-galactosidase plasmid DNA (in the PSI® vector), 50 $\mu$L of DMEM, and 15 $\mu$L of Superfect®. This mixture was then augmented with additional DMEM (with 10% calf serum and 1% penicillin/streptomycin/glutamine) sufficient to incubate each well with 50 $\mu$L of the transfection mixture. Cells were transfected for 12 to 16 hours at 37° C. in a humidified environment supplemented with 5% $CO_2$, after which time the media was replaced by DMEM with 2% cyto-SF3 (Kemp Biotechnologies, Inc.) containing variable amounts of the compounds being tested.

Cells were grown in a humidified environment at 37° C. with 5% $CO_2$ for five days prior to visualization of β-galactosidase activity by replacing the media with the β-galactosidase substrate o-nitrophenyl-β-D-galactopyranoside (substantially as described in U.S. Pat.

No. 5,707,798). All data were obtained by measuring the change in absorbance at 420 nm using an automated plate reader (BioTek EL 310). EC50 values were calculated using the equation: r=A+B(x/(x+c)), where A=minimum response, B=maximum response minus minimum response, c=EC50, r=response, and x=concentration of ligand. Curves were generated by least-squares fit using the program Kaleida-Graph® (Abelbeck Software).

Since constitutive activity may be erroneously measured if experiments are conducted in the presence of minute amounts of agonist, a number of control experiments were performed to rule out the possibility that serotonin was present in the media. Firstly, only synthetic sera were used (cyto-SF3), because bovine calf serum may contain various monoamines or related receptor agonists. Second, experiments in which the amount of synthetic sera was about 2–5 times that routinely used did not result in a measurable increase in constitutive activity (data not shown). In addition, using other serotonin receptor subtypes in which constitutive activity has been measured (5-HT2B) revealed compounds that are neutral antagonists and others that are inverse agonists, arguing that competition for endogenous serotonin is not occurring (otherwise, all compounds would appear to be inverse agonists).

The results of this analysis of the 5-HT2A receptor are presented in FIG. 1, as a representative pharmacological profile as determined by R-SAT.

Based on the results obtained in this analysis, it was concluded that 1) the 5-HT2A receptor is functionally active in R-SAT, and that the data obtained are in agreement with previously published binding assays (C. A. Stockmneier et al., J. Pharm Exper. Ther. 266(3), 1993, pp. 1374–1384).

2) expression of 5-HT2A receptors using the PSI® vector results in the detection of constitutive activity. Under these experimental conditions, ritanserin inhibits receptor signaling below baseline (no drug) values, i.e. it is an inverse agonist (note ritanserin values in FIG. 1).

3) increasing the amount of DNA used for transfection increased the basal activity of the 5-HT2A receptor (5% constitutive activity at 5 ng/well vs. 11% constitutive activity at 50 ng/well; data not shown).

Upon detecting constitutive signaling with the 5-HT2A receptor, high DNA concentrations were subsequently used to augment basal responses and facilitate pharmacological analysis of inverse agonists. All subsequent studies utilized 50 ng/well of 5-HT2A receptor DNA. FIG. 2 shows the dose response relationship for ritanserin as a representative 5-HT2A receptor inverse agonist.

R-SAT was configured to assay simultaneously for compounds that exhibit both agonism and inverse agonism at this receptor subtype. Multiple 96-well plates of NIH 3T3 cells were transfected with 50 ng/well of 5-HT2A receptor DNA and screened against a 640-compound library of medically relevant drugs (RBI Inc, Natick, Mass.). All compounds were screened at concentrations of 300–500 nM, serotonin (1 μM) was used as a reference agonist, and ritanserin (1 μM) was used as a reference inverse agonist. The results of this screen for inverse agonism (for compounds with greater than 40% inhibition) at the 5-HT2A receptor are shown in Table 1 below.

TABLE 1

Screen for Inverse Agonism at 5-HT2A Receptors

| % INHIBITION | COMPOUND |
| --- | --- |
| 96 | TRIFLUPERIDOL |
| 92 | PIRENPIRONE |
| 90 | RITANSERIN |
| 87 | RISPERIDONE |
| 84 | BUTACLAMOL |
| 82 | SPIPERONE |
| 82 | KETANSERIN |
| 79 | MIANSERIN |
| 79 | METHIOTHEPIN |
| 77 | LOXAPINE |
| 76 | OCTOCLOTHEPIN |
| 75 | Mdl 26,630 trihcl |
| 75 | TRIFLOUPERAZINE |
| 75 | CINANSERIN |
| 74 | Dag kinase inhibitor |
| 69 | JL-18 (CLOZAPINE) |
| 68 | AMOXAPINE |
| 66 | CYPROHEPTADINE |
| 65 | CHLORPROMAZINE |
| 62 | METERGOLINE |
| 61 | FLUPHENAZINE |
| 57 | FLUSPIRILINE |
| 56 | THIORIDAZINE |
| 53 | Benztropine |
| 53 | 5-hydroxy-Ltryptophan |
| 52 | Promethazine |
| 52 | CLOZAPINE |
| 51 | Physostigmine |
| 45 | CIS-FLUPENTIXOL |
| 42 | PIMOZIDE |

In Table 1, all data are derived from the mean of duplicate determinations for each test compound, and are presented as a percentage inhibition referenced to ritanserin (90–100%). The data include all compounds detected in the screen that displayed a greater than 40% inhibition from basal, no drug, levels. All compounds that are known serotonergic drugs are italicized, and all drugs with known anti-psychotic activity are presented in bold.

The results of this screen are significant in that:

1) The screen identified nearly every antipsychotic drug in the compound library (18/19 at 30% inhibition or greater), documenting that these drugs are actually inverse agonists (not antagonists) at this receptor subtype.

2) There is selectivity to this interaction, as multiple classes of other neuropsychiatric agents (e.g., antidepressants and anticonvulsants) represented in the library are not inverse agonists at this receptor subtype.

3) The R-SAT technology is amenable to screening compounds for inverse agonism at the 5-HT2A receptor.

4) The R-SAT technology is amenable to screening individuals for constitutively activating mutations of the 5-HT2A receptor in an analogous manner to that presented above.

Having discovered that antipsychotics are inverse agonists of the 5-HT2A receptor, a detailed pharmacological analysis of many of these agents was performed to establish their potency and efficacy. FIG. 3 shows the dose response curves for two known antipsychotics, the typical agent haloperidol, and the atypical agent risperidone. Table 2 is a compilation of this detailed pharmacological analysis presented as negative log EC50 values.

TABLE 2

Potency of Antipsychotics as Inverse Agonists at the 5-HT2A Receptor

| DRUG | Negative LOG EC50 |
|---|---|
| Sertindole | 10.12 +/− 0.18 |
| Tefludazine | 9.02 +/− 0.21 |
| Risperidone | 8.81 +/− 0.05 |
| Spiperone | 8.70 +/− 0.07 |
| Pimozide | 8.65 +/− 0.04 |
| Amoxapine | 8.64 +/− 0.13 |
| Loxapine | 8.49 +/− 0.07 |
| Butaclamol | 8.49 +/− 0.19 |
| Fluspirilene | 8.49 +/− 0.14 |
| Clozapine | 8.17 +/− 0.19 |
| Olanzapine | 8.17 +/− 0.07 |
| JL-18 | 8.11 +/− 0.13 |
| Cis-Flupentixol | 8.04 +/− 0.10 |
| Fluphenazine | 7.85 +/− 0.10 |
| Chlorpromazine | 7.70 +/− 0.11 |
| Triflouperidol | 7.59 +/− 0.09 |
| Thioridazine | 7.02 +/− 0.18 |
| Triflouperazine | 6.76 +/− 0.19 |
| Trans-Flupentixol | 6.77 +/− 0.21 |
| Haloperidol | 6.79 +/− 0.03 |
| Thiothixene | 6.43 +/− 0.11 |
| Sulpiride | NO EFFECT |
| Remoxipride | AGONIST |
| Molindone | AGONIST |

Table 2 above provides the molar negative log EC50s for inhibition of constitutive activity derived from the mean of three separate dose response experiments (+/− standard error). Antipsychotics that are generally considered atypical are highlighted in bold.

These data allow one to draw the following conclusions regarding antipsychotics as inverse agonists of the 5-HT2A receptor:

1) Nearly all antipsychotics tested are potent inverse agonists of the 5-HT2A receptor. No similar activity of these drugs as inverse agonists at other potentially relevant monoamine receptors (5-HT1A, 5-HT1B, 5-HT2C, Dopamine D1, D2, D3, and D5, α-1B adrenergic, and muscarinic m5 receptors) has been noted (T. A. Spalding et al., supra; Nilsson, C. L., supra; Hall, D. A. and Strange, P. G., supra, E. L. Barker et al., supra; A. Newman-Tancredi et al., *Brit. Jour. of Pharm.* 120, pp. 737–739; P. A. Pauwels and F. C. Colpaert, *Biochem. Pharm.* 50(10), pp. 1651–1658; and D. R. Thomas et al., *J. of Receptor and Signal Transduction Research* 15(1–4), pp. 199–211). The correlation between this singular molecular pharmacological mechanism and efficacy of a drug as an antipsychotic suggests that this is a findamental mechanism of action of this class of drug.

2) The atypical antipsychotic agents are amongst the most potent of 5-HT2A receptor inverse agonists; thus, potent and selective 5-HT2A inverse agonism should be a property of novel antipsychotic drugs with improved clinical profiles.

3) Since antipsychotics as a class possess the intrinsic activity to reduce constitutive signal transduction mediated by the 5-HT2A receptors, any condition that favors increased basal activity of this receptor may be contributory to, or causative of, psychosis and/or schizophrenia.

It is apparent that the singular molecular property of inverse agonism at the 5-HT2A receptor is common to nearly all compounds with efficacy as an antipsychotic. To further support the uniqueness of this correlation, a large series of antipsychotics were pharmacologically profiled against the human 5-HT2C receptor. This receptor was chosen because: 1) it is genetically and pharmacologically related to the 5-HT2A receptor, 2) the receptor RNA and protein are expressed in human brain regions critical to higher cognitive functioning, and 3) some evidence exists to support the notion that antagonism of this receptor is relevant to the mechanism of action of antipsychotic drugs. The wild type human 5-HT2C receptor was PCR-cloned from human cortical cDNA by standard molecular biological techniques familiar to those skilled in the art. The receptor construct was subdloned into the PSI® mammalian expression vector, and verified by DNA sequencing. Transfection of 50 ng per well of receptor DNA (identical to the amount used for 5-HT2A assays) revealed readily measurable constitutive activity. Thirty-six antipsychotics were pharmacologically assayed against the 5-HT2C receptor as both agonists and inverse agonists. Table 3 reports the negative log EC50 for these compounds as inverse agonists at both the 5-HT2A and 5-HT2C receptors.

TABLE 3

Potency of Antipsychotics as Inverse Agonists at 5-HT2A and 5-HT2C Receptors

| DRUG EC50 | 5-HT2A Receptor Negative Log EC50 | 5-HT2C Receptor Negative Log |
|---|---|---|
| Sertindole | 10.12 +/− 0.18 | 7.64 +/− 0.42 |
| Octoclothepin | 9.74 +/− 0.98 | 8.52 +/− 0.56 |
| Tefludazine | 9.02 +/− 0.21 | 8.28 +/− 0.49 |
| Respiridone | 8.81 +/− 0.05 | <5.0 |
| Tiospirone | 8.74 +/− 0.67 | 6.29 +/− 0.53 |
| Spiperone | 8.70 +/− 0.07 | No Intrinsic Activity |
| Pimozide | 8.65 +/− 0.04 | No Intrinsic Activity |
| Amoxapine | 8.64 +/− 0.13 | 6.92 +/− 0.34 |
| Clothiapine | 8.55 +/− 1.09 | 6.32 +/− 0.57 |
| Butaclamol | 8.49 +/− 0.19 | No Intrinsic Activity |
| Loxapine | 8.49 +/− 0.07 | 6.30 +/− 0.32 |
| Fluspirilene | 8.19 +/− 0.14 | No Intrinsic Activity |
| Clozapine | 8.17 +/− 0.19 | 6.60 +/− 0.64 |
| Olanzapine | 8.17 +/− 0.07 | 6.36 +/− 0.47 |
| JL-18 | 8.11 +/− 0.13 | 6.09 +/− 0.45 |
| Cis-Flupentixol | 8.04 +/− 0.10 | No Intrinsic Activity |
| Fluphenazine | 7.85 +/− 0.10 | <5.0 |
| Amperozide | 7.80 +/− 0.82 | No Intrinsic Activity |
| Chlorproethizene | 7.70 +/− 0.33 | <5.0 |
| Chlorpromazine | 7.70 +/− 0.11 | No Intrinsic Activity |
| Triflouperidol | 7.59 +/− 0.09 | <5.0 |
| Perlapine | 7.52 +/− 0.49 | 5.89 +/− 1.17 |
| Promazine | 7.10 +/− 1.27 | Agonist |
| Moperone | 7.03 +/− 0.59 | No Intrinsic Activity |
| Thioridazine | 7.02 +/− 0.18 | No Intrinsic Activity |
| Mesioridazine | 7.00 +/− 0.30 | No Intrinsic Activity |
| Melperone | 6.96 +/− 0.56 | No Intrinsic Activity |
| Haloperidol | 6.79 +/− 0.03 | No Intrinsic Activity |
| Trans-Flupentixol | 6.77 +/− 0.21 | 5.55 +/− 0.37 |
| Triflouperazine | 6.76 +/− 0.19 | No Intrinsic Activity |
| Bromperidol | 6.66 +/− 0.76 | No Intrinsic Activity |
| Prothypendyl | 6.60 +/− 0.44 | Agonist |
| Quietapine | 6.57 +/− 0.80 | No Intrinsic Activity |

TABLE 3-continued

Potency of Antipsychotics as Inverse Agonists at 5-HT2A and 5-HT2C Receptors

| DRUG EC50 | 5-HT2A Receptor Negative Log EC50 | 5-HT2C Receptor Negative Log |
|---|---|---|
| Thiothixene | 6.43 +/− 0.11 | No Intrinsic Activity |
| Sulpiride | No Intrinsic Activity | No Intrinsic Activity |
| Remoxipride | AGONIST | No Intrinsic Activity |
| Molindone | AGONIST | No Intrinsic Activity |

The following conclusions can be drawn from this data:
1) The correlation between inverse agonism and efficacy as an antipsychotic is apparent at the 5-HT2A receptor (33 of 36 compounds), but does not exist at the 5-HT2C receptor (12 of 36 compounds).
2) High potency inverse agonism at the 5-HT2A receptor is a property that many of the "atypical" antipsychotics share, yet no such correlation between compounds with improved clinical characteristics ("atypicals") and 5-HT2C receptor intrinsic activity can be drawn.

To identify novel compounds as potential antipsychotic drugs, the 5-HT2A inverse agonist R-SAT assay was formatted to conduct high-throughput screening of large libraries of organic compounds. For these purposes, the constitutive basal response of the 5-HT2A receptor was augmented by the addition of the alpha subunit of the heterotrimeric G-protein Gq into the transfection mixtures. Gq is the signaling molecule utilized by the 5-HT2A receptor to functionally signal in cells, and coexpressing Gq with other GPCR's has been previously shown to constitutively activate receptors in this class (Burstein, E. S., et al., *FEBS Lett.* 363, 1995, pp. 261–263).

The 5-HT2A inverse agonist assay was used to screen 135,000 organic compounds for 5-HT2A inverse agonist activity. The compounds examined were from a library of structurally diverse organic molecules with an average molecular weight of 350 daltons. The compounds were dissolved in DMSO and plated onto microtiter plates with one compound in each well and either 96 or 384 compounds on each plate. The compounds were diluted to a concentration of 3000 nM, incubated in the presence of transfected cells for a period of five days, after which time beta-galactosidase activity was measured to determine the functional response of potential inverse agonists. These compounds were also screened against the muscarinic m5 receptor, in an analogous fashion, to provide a measure of selectivity for the active compounds.

Of the 135,000 compounds tested in this manner, 511 were identified that repressed the 5-HT2A basal activity in replicate samples greater than 50% of that observed with the control inverse agonist, 100 nM ritanserin. Of the 511 compounds that repressed 5-HT2A constitutive activity greater than 50% at 3000 nM, 322 compounds repressed significantly at 300 nM as well. Of these, 252 compounds displayed greater than 10-fold selectivity for 5-HT2A inverse agonism compared to inverse agonism at the muscarinic m5 receptor.

Of the 252 5-HT2A selective compounds, 111 are related in structure to the known antipsychotic haloperidol, and 64 compounds are structurally related to the tricyclic antidepressants compounds with known antipsychotic activity. Examples of these are the compound AC121394 in the haloperidol class, and compound AC116399 in the tricyclic class (see FIG. 4). The successful screening of compounds with 5-HT2A inverse activity that are related in structure to known antipsychotics is a direct demonstration that one can identify compounds with potentially improved antipsychotic activity.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The disclosures of all references cited herein are incorporated by reference in their entireties.

What is claimed is:

1. A method of identifying a compound with antipsychotic activity, the method comprising:
   (a) contacting a 5-HT2A receptor having wild type constitutive activity with at least one test compound; and
   (b) determining any decrease in basal activity of the 5-HT2A receptor having wild type constitutive activity, wherein a decrease in basal activity of the 5-HT2A receptor identifies a compound with antipsychotic activity.

2. The method of claim 1, wherein the 5-HT2A receptor is human.

3. A method of identifying a compound with antipsychotic activity, the method comprising:
   (a) culturing cells which express a 5-HT2A receptor having wild type constitutive activity;
   (b) incubating the cells with at least one test compound; and
   (c) determining any decrease in basal activity of the 5-HT2A receptor having wild type constitutive activity, wherein a decrease in basal activity of the 5-HT2A receptor identifies a compound with antipsychotic activity.

4. The method of claim 3, wherein the 5-HT2A receptor is human.

5. The method of claim 3, wherein the cells of step (a) overexpress said 5-HT2A receptor.

6. The method of claim 3, wherein the identified antipsychotic compound is selective for the 5-HT2A receptor.

7. A method of identifying a compound useful in treating the symptoms of disease or disorder associated with constitutive activity of the 5-HTA receptor, the method comprising:
   (a) contacting a 5-HT2A receptor having wild type constitutive activity with at least one test compound; and
   (b) determining any decrease in basal activity of the 5-HT2A receptor having wild type constitutive activity, wherein a decrease in basal activity of the 5-HT2A receptor identifies a compound useful in treating the symptoms of disease or disorder associated with constitutive activity of the 5-HTA receptor.

8. The method of claim 7, wherein the 5-HT2A receptor is human.

9. The method of claim 7, wherein the disease or disorder is psychosis.

10. The method of claim 7, wherein the disease or disorder is schizophrenia.

11. The method of claim 7, wherein said symptoms are selected from the group consisting of: hallucination, delusion, emotional withdrawal, apathy and poverty of speech.

* * * * *